United States Patent
Bürke et al.

(10) Patent No.: US 10,064,708 B2
(45) Date of Patent: Sep. 4, 2018

(54) BLANK FOR DENTAL PURPOSES

(71) Applicant: Ivoclar Vivadent AG, Schaan (LI)

(72) Inventors: Harald Bürke, Frastanz (AT); Diana Tauch, Haag (CH); Marcel Schweiger, Chur (CH); Wolfram Höland, Schaan (LI); Christian Ritzberger, Grabs (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 177 days.

(21) Appl. No.: 14/762,612

(22) PCT Filed: Feb. 7, 2014

(86) PCT No.: PCT/EP2014/052470
§ 371 (c)(1),
(2) Date: Jul. 22, 2015

(87) PCT Pub. No.: WO2014/124879
PCT Pub. Date: Aug. 21, 2014

(65) Prior Publication Data
US 2015/0374465 A1    Dec. 31, 2015

(30) Foreign Application Priority Data

Feb. 12, 2013 (EP) .................... 13154979

(51) Int. Cl.
*A61C 13/08* (2006.01)
*A61C 8/00* (2006.01)
(Continued)

(52) U.S. Cl.
CPC .............. *A61C 13/082* (2013.01); *A61C 5/70* (2017.02); *A61C 5/73* (2017.02); *A61C 5/77* (2017.02); *A61C 8/0012* (2013.01); *A61C 13/0004* (2013.01); *A61C 13/0022* (2013.01); *A61C 13/083* (2013.01); *B32B 7/02* (2013.01);
(Continued)

(58) Field of Classification Search
None
See application file for complete search history.

(56) References Cited

U.S. PATENT DOCUMENTS

| | | | |
|---|---|---|---|
| 2,684,911 A | 7/1954 | Stookey |
| 3,006,775 A | 10/1961 | Chen |
| 3,022,180 A | 2/1962 | Morrissey |
| 3,161,528 A | 12/1964 | Eppler |
| 3,252,778 A | 5/1966 | Goodman et al. |
| 3,804,608 A | 4/1974 | Gaskell et al. |
| 3,816,704 A | 6/1974 | Borom et al. |

(Continued)

FOREIGN PATENT DOCUMENTS

| | | |
|---|---|---|
| CA | 2163792 A1 | 12/1994 |
| CA | 2213390 A1 | 3/1998 |

(Continued)

OTHER PUBLICATIONS

Apel, E., et al., "Influence of ZrO2 on the crystallization and properties of lithium disilicate glass-ceramics derived from multi-component system", Journal of European Ceramic Society, 2007, 27, 1571-1577.

(Continued)

*Primary Examiner* — David R Sample
(74) *Attorney, Agent, or Firm* — Ann M. Knab; Thad McMurray (57) ABSTRACT

Blanks for dental purposes are described which have at least two layers, bonded to one another, of lithium silicate glasses and glass ceramics, wherein the layers differ in color and the layers are monolithic.

35 Claims, 6 Drawing Sheets

(51) Int. Cl.
*A61C 13/083* (2006.01)
*A61C 13/00* (2006.01)
*C03C 10/00* (2006.01)
*B32B 7/02* (2006.01)
*C03B 32/02* (2006.01)
*C03B 23/20* (2006.01)
*C03C 3/097* (2006.01)
*B32B 17/06* (2006.01)
*A61C 5/73* (2017.01)
*A61C 5/77* (2017.01)
*C03C 4/00* (2006.01)
*C03C 8/24* (2006.01)
*C03C 27/10* (2006.01)
*A61C 5/70* (2017.01)

(52) U.S. Cl.
CPC .............. *B32B 17/06* (2013.01); *C03B 23/20* (2013.01); *C03B 32/02* (2013.01); *C03C 3/097* (2013.01); *C03C 4/0021* (2013.01); *C03C 8/24* (2013.01); *C03C 10/0009* (2013.01); *C03C 10/0027* (2013.01); *C03C 27/10* (2013.01); *B32B 2535/00* (2013.01)

(56) References Cited

U.S. PATENT DOCUMENTS

| | | | |
|---|---|---|---|
| 3,977,857 A | 8/1976 | Mattox | |
| 4,155,888 A | 5/1979 | Mooth | |
| 4,189,325 A | 2/1980 | Barrett et al. | |
| 4,414,282 A | 11/1983 | McCollister et al. | |
| 4,473,653 A | 9/1984 | Rudoi | |
| 4,480,044 A | 10/1984 | McAlinn | |
| 4,515,634 A | 5/1985 | Wu et al. | |
| 4,671,770 A | 6/1987 | Bell et al. | |
| 4,963,707 A | 10/1990 | Zyokou et al. | |
| 4,977,114 A | 12/1990 | Horinouchi et al. | |
| 5,176,961 A | 1/1993 | Crooker et al. | |
| 5,219,799 A | 6/1993 | Beall et al. | |
| 5,507,981 A | 4/1996 | Petticrew | |
| 5,628,564 A | 5/1997 | Nenyei et al. | |
| 5,691,256 A | 11/1997 | Taguchi et al. | |
| 5,698,482 A | 12/1997 | Frank et al. | |
| 5,702,514 A | 12/1997 | Petticrew | |
| 5,707,777 A | 1/1998 | Aoai et al. | |
| 5,872,069 A | 2/1999 | Abe | |
| 5,874,376 A | 2/1999 | Taguchi et al. | |
| 5,938,959 A | 8/1999 | Wang | |
| 5,968,856 A | 10/1999 | Schweiger et al. | |
| 6,048,589 A | 4/2000 | Suzuki | |
| 6,066,584 A | 5/2000 | Krell et al. | |
| 6,095,682 A | 8/2000 | Hollander et al. | |
| 6,106,747 A | 8/2000 | Wohlwend | |
| 6,121,175 A | 9/2000 | Drescher et al. | |
| 6,157,004 A | 12/2000 | Bizzio | |
| 6,163,020 A | 12/2000 | Bartusch et al. | |
| 6,174,827 B1 | 1/2001 | Goto et al. | |
| 6,252,202 B1 | 6/2001 | Zychek | |
| 6,267,595 B1 | 7/2001 | Gratz | |
| 6,270,876 B1 | 8/2001 | Abe et al. | |
| 6,287,121 B1 | 9/2001 | Guiot et al. | |
| 6,342,458 B1 | 1/2002 | Schweiger et al. | |
| 6,376,397 B1 | 4/2002 | Petticrew | |
| 6,379,593 B1 | 4/2002 | Datzmann et al. | |
| 6,420,288 B2 | 7/2002 | Clausbruch et al. | |
| 6,441,346 B1 | 8/2002 | Zychek | |
| 6,455,451 B1 | 9/2002 | Brodkin et al. | |
| 6,485,849 B2 | 11/2002 | Petticrew | |
| 6,514,893 B1 | 2/2003 | Schweiger et al. | |
| 6,517,623 B1 | 2/2003 | Brodkin et al. | |
| 6,593,257 B1 | 7/2003 | Nagata et al. | |
| 6,802,894 B2 | 10/2004 | Brodkin et al. | |
| 6,818,573 B2 | 11/2004 | Petticrew | |
| 7,162,321 B2 | 1/2007 | Luthardt et al. | |
| 7,316,740 B2 | 1/2008 | Rheinberger et al. | |
| 7,452,836 B2 | 11/2008 | Apel et al. | |
| 7,655,586 B1 | 2/2010 | Brodkin et al. | |
| 7,806,694 B2 | 10/2010 | Brodkin et al. | |
| 7,816,291 B2 | 10/2010 | Schweiger et al. | |
| 7,867,930 B2 | 1/2011 | Apel et al. | |
| 7,867,933 B2 | 1/2011 | Apel et al. | |
| 7,871,948 B2 | 1/2011 | Apel et al. | |
| 7,892,995 B2 | 2/2011 | Castillo | |
| 7,993,137 B2 | 8/2011 | Apel et al. | |
| 8,042,358 B2 | 10/2011 | Schweiger et al. | |
| 8,047,021 B2 | 11/2011 | Schweiger et al. | |
| 8,444,756 B2 | 5/2013 | Schweiger et al. | |
| 2001/0006174 A1 | 7/2001 | Brennan | |
| 2001/0031446 A1 | 10/2001 | Petticrew | |
| 2002/0010063 A1 | 1/2002 | Schweiger et al. | |
| 2002/0022563 A1 | 2/2002 | Schweiger et al. | |
| 2002/0031670 A1 | 3/2002 | Goto et al. | |
| 2002/0035025 A1 | 3/2002 | Schweiger et al. | |
| 2002/0160694 A1 | 10/2002 | Wood et al. | |
| 2003/0073563 A1 | 4/2003 | Brodkin | |
| 2003/0132539 A1* | 7/2003 | Althoff | A61C 13/0003 264/16 |
| 2004/0182538 A1 | 9/2004 | Lambrecht | |
| 2005/0098064 A1 | 5/2005 | Schweiger et al. | |
| 2005/0127544 A1 | 6/2005 | Brodkin et al. | |
| 2006/0082033 A1 | 4/2006 | Hauptmann et al. | |
| 2006/0257823 A1 | 11/2006 | Pfeiffer et al. | |
| 2006/0257824 A1 | 11/2006 | Pfeiffer et al. | |
| 2007/0023971 A1 | 2/2007 | Saha et al. | |
| 2007/0042889 A1* | 2/2007 | Apel | C03B 32/02 501/5 |
| 2008/0120994 A1 | 5/2008 | Schweiger et al. | |
| 2008/0199823 A1 | 8/2008 | Miller | |
| 2009/0023574 A1 | 1/2009 | Holand et al. | |
| 2009/0038344 A1 | 2/2009 | Apel et al. | |
| 2009/0038508 A1 | 2/2009 | Apel et al. | |
| 2009/0042166 A1 | 2/2009 | Craig et al. | |
| 2009/0136901 A1 | 5/2009 | Cadario et al. | |
| 2009/0256274 A1 | 10/2009 | Castillo | |
| 2009/0258778 A1 | 10/2009 | Castillo | |
| 2010/0083706 A1 | 4/2010 | Castillo | |
| 2011/0236857 A1 | 9/2011 | Rheinberger et al. | |
| 2011/0256409 A1 | 10/2011 | Ritzberger et al. | |
| 2011/0319254 A1 | 12/2011 | Ritzberger et al. | |
| 2012/0094822 A1 | 4/2012 | Castillo et al. | |
| 2012/0148988 A1 | 6/2012 | Castillo et al. | |
| 2012/0248642 A1 | 10/2012 | Ritzberger et al. | |
| 2012/0309607 A1 | 12/2012 | Durschang | |
| 2013/0069264 A1 | 3/2013 | Giordano | |
| 2014/0141960 A1 | 5/2014 | Borczuch-Laczka et al. | |

FOREIGN PATENT DOCUMENTS

| | | |
|---|---|---|
| CA | 2252660 A1 | 5/1999 |
| DE | 2451121 A1 | 5/1975 |
| DE | 4303458 C1 | 1/1994 |
| DE | 102005028637 A1 | 12/2006 |
| EP | 1152641 A2 | 11/2001 |
| EP | 1505041 A1 | 2/2005 |
| EP | 1688397 A1 | 8/2006 |
| EP | 1688398 A1 | 8/2006 |
| GB | 752243 A | 7/1956 |
| GB | 2284655 A | 6/1995 |
| JP | H10323354 A | 12/1998 |
| JP | 1174418 | 3/1999 |
| JP | 2005-062832 A | 3/2005 |
| JP | 2012254898 A | 12/2012 |
| WO | 2007028787 A1 | 3/2007 |
| WO | 2008083358 A1 | 7/2008 |
| WO | WO 2013086187 A1 * | 6/2013 ........... A61K 6/0273 |

OTHER PUBLICATIONS

Durschang, Dr. Bernhard, "Report of Results", Fraunhofer Institute for Silicate Research ISC Glass and Mineral Materials, 2015.

(56) References Cited

OTHER PUBLICATIONS

McMillan, P.W., et al., "The Structure and Properties of a Lithium Zinc Silicate Glass-Ceramic", Journal of Material Science 1966, I. 269-279.

Deubener, J., et al., "Induction time analysis of nucleation and crystal grown in di- and metasilicate glasses", Journal of Non-Crystalline Solids 1993, 163, 1-12.

Holand, W., et al., "Glass-ceramic technology", American Chemical Society 2002, Westerville OH, USA.

Holand, W., et al., "Control of nucleation in glass ceramics", Phil. Trans. Soc. Land. A 2003, 361, 575-589.

Holand, W., et al., "Principles and phenomena of bioengineering with glass-ceramics of dental restoration", Journal of the European Ceramics Society 2007, 27, 1571-1577.

Ivoclar Vivadent, Inc., IPS e.max lithium disilicate, 627329, Rev. Feb. 2009.

Borom, M.P., et al., "Strength and Microstructure in Lithium Disilicate Glass Ceramics", J. Am. Ceram. Soc., 1975,58, 385-391.

Von Clausbruch, et al., "Effect of ZnO on the Crystallization, Microstructure, and Properties of Glass-Ceramics in the $SiO_2$—$Li_2O$—$K_2O$—$P_2O_5$ System," Glastech. Ber. Glass Sci. Technol. 74(8):223-229(2001).

Von Clausbruch, et al., "Effect of P2O5 on the Crystallization and Microstructure of Glass-Ceramics in the $SiO_2$—$Li_2O$—$Zn$)-$P_2O_5$ System," Glastech. Ber. Glass Sci. Technol. 74(8):223-229(2001).

Stookey, S.D., "Chemical Machining of Photosensitive Glass," Ind. Eng. Chem. 45:115-118 (1993).

Oliveria et al., "Sintering and Crystallization of a GlassPowder in the $Li_2O$—$ZrO_2$—$SiO_2$ System," J. Amer. Ceramic Soc. 81(3):777-780 (1998).

Montedo, et al., "Low Thermal Expansion Sintered LZSA Glass-Ceramics," American Ceramic Society Bulletin, vol. 87, No. 7, pp. 34-40.

Giassi, et al., "Injection Moulding of $LiO_2$—$ZrO_2$—$SiO_2$—$Al_2O_3$ (LZSA) Glass Ceramics," Glass Technol., 46(3), 277-280 (2005).

http://en.wikipedia.org/wiki/Nucleation ; Sep. 20, 2012.

International Preliminary Report on Patentability of PCT/EP2014/052470, dated Aug. 18, 2015, 7 pages.

\* cited by examiner

BLANK FOR DENTAL PURPOSES

CROSS-REFERENCE TO RELATED APPLICATIONS

This application is a National Stage application of International Patent Application No. PCT/EP2014/052470 filed on Feb. 7, 2014, which claims priority to European Patent Application No. 13154979.2 filed on Feb. 12, 2013, the disclosures of which are incorporated herein by reference in their entirety.

The invention relates to a blank for dental purposes with which the optical properties of natural tooth material can be very well imitated and which, because of its properties, is suitable in particular for easily producing highly aesthetic dental restorations with very good mechanical properties.

It represents a great challenge to produce blanks which meet the manifold requirements for a use in the field of dental engineering. Such blanks are intended not only to be easy to produce but they are also intended to be capable of being shaped easily and still result in high-strength restorations. Finally, the blanks themselves are intended to already have an appearance which is close to that of the natural tooth material in order that a costly subsequent veneering of the restorations can be dispensed with.

Blanks for use in dentistry are known from the state of the art.

DE 197 14 178 A1 describes multicoloured shaped bodies made of ceramic or plastic from which dental restorations can be produced by further machining. In particular a leucite-containing glass ceramic is used as ceramic material. To produce the shaped bodies different coloured powders or granular materials of the starting materials are poured into a compacting die and pressed. The shaped body is also sintered for strengthening and, in its strengthened form, further processed to form a dental restoration by means of CAD/CAM processes or copy-milling.

Single-coloured blanks based on lithium metasilicate glass ceramics which, because of their relative low strength, can be easily machined and converted by heat treatment to high-strength dental restorations based on lithium disilicate glass ceramic, are known from DE 103 36 913 A1.

EP 1 859 757 A2 discloses multicoloured blanks based on $ZrO_2$ which are obtained by pressing differently coloured layers of powder or granular material and pre-sintering. The resulting blank is shaped to a dental shaped part by milling and grinding. The milling process must be carried out such that the dental pre-shaped part is enlarged in order to take into account the shrinkage of the shaped part in the subsequent dense-sintering.

EP 2 065 012 A1 describes the production of dental restorations with colour and opacity gradients which give a natural impression, made from ceramic shaped bodies which have differently coloured areas in their volume. The shaped bodies are pressed into a mould cavity using a specially designed channel system under the action of pressure and heat in order to form the dental restoration. The special channel system ensures the desired distribution of the differently coloured areas in the volume of the restoration. A machining of the shaped bodies to form the restoration is not described.

EP 1 900 341 A1 discloses shaped bodies of several differently coloured layers with a special sequence of layers in order that the colour transition between the layers is not perceptible. The shaped bodies are produced by dry pressing differently coloured glass ceramic powders coated on top of one another, debinding and sintering. Dental restorations can be produced from these shaped bodies by means of CAD/CAM processes.

The known multicoloured blanks made of layers of powder or granular material, however, also require after shaping into a dental restoration a sintering step to achieve the high strength imperative for a dental restoration. However, this sintering is associated with a marked shrinkage which must be taken into account by using enlarged preforms, which complicates the process. The known blanks also cannot in every case be processed to form the desired dental restorations by machining or they have too high a strength for such a processing, which leads to an excessive wear of the grinding and milling tools used.

According to the invention these problems are to be avoided. In particular the object of the invention is to make available a blank with which the optical appearance of natural tooth material can be very well imitated, which can easily be given, by machining, the shape of the desired dental restoration and which, after shaping, can be converted without substantial shrinkage, to a precise and high-strength dental restoration.

BRIEF DESCRIPTION OF THE DRAWINGS

Further advantages, details and features can be seen from the following description and drawings wherein.

The blank according to the invention for dental purposes is characterized in that it has at least 2 layers, bonded to one another, of
- lithium silicate glass,
- lithium silicate glass with nuclei or
- lithium metasilicate glass ceramic, wherein the layers differ in colour and the layers are monolithic.

By differences in colour are also meant differences in translucence, opalescence or fluorescence. The colour can be characterized in particular by its Lab value or by a shade guide customary in the dental industry.

It is preferred that the layers consist of lithium silicate glass, lithium silicate glass with nuclei or lithium metasilicate glass ceramic.

The term "monolithic" refers to layers which are continuous and thus differ from discontinuous layers such as layers of particles, e.g. layers of powder or granular material. The monolithic layers used according to the invention can also be called solid or bulk layers of glasses and glass ceramics.

The presence of monolithic layers in the blank according to the invention is also responsible for the fact that it is possible to convert it to the desired high-strength dental restoration by heat treatment without substantial shrinkage. By contrast, the discontinuous layers present in conventional blanks, such as pressed layers of powders or granular materials, must still be densely-sintered in order to produce the final dental restoration. However, this dense-sintering leads to a considerable shrinkage. To produce precisely fitting dental restorations, therefore, firstly an enlarged preform of the restoration must be produced and this enlarged preform is then densely-sintered. However, such a procedure is sophisticated and prone to errors. It also requires in the first place that the enlargement factor to be chosen in each case is precisely determined, which depends, inter alia, on the exact sintering conditions and the type of blank used.

The blank according to the invention has at least 2 monolithic layers which differ in colour. In a preferred embodiment the blank contains 2 to 10, in particular 2 to 8, such layers. It is easily possible with these different layers to imitate the visual properties of the different regions of a natural tooth material to be replaced. Therefore, the blank according to the invention succeeds in satisfying the ever-increasing demand for starting materials for dental prostheses which meet very high optical requirements.

The layers have preferably a thickness of 0.5 to 10.0 and in particular of 1.0 to 8.0 mm.

The blank has monolithic layers of lithium silicate glass, lithium silicate glass with nuclei or lithium metasilicate glass ceramic.

The lithium silicate glass is usually prepared by melting suitable starting materials. This glass can be converted to the lithium silicate glass with nuclei by heat treatment. The nuclei are those used for the crystallization of lithium metasilicate and/or lithium disilicate. The lithium silicate glass with nuclei can be converted to the lithium metasilicate glass ceramic by heat treatment.

Finally, it is possible to convert the lithium metasilicate glass ceramic to high-strength lithium disilicate glass ceramic by further heat treatment. The lithium silicate glass, the lithium silicate glass with nuclei and the lithium metasilicate glass ceramic are therefore precursors of the lithium disilicate glass ceramic.

In a preferred embodiment the blank according to the invention has monolithic layers of lithium silicate glass with nuclei or monolithic layers of lithium metasilicate glass ceramic. Because of its relatively low strength such a blank can be given the shape of the desired dental restoration particularly easily by machining.

Furthermore, a blank is preferred in which the lithium metasilicate glass ceramic comprises lithium metasilicate as main crystal phase and in particular comprises more than 5 vol.-%, preferably more than 10 vol.-% and particularly preferably more than 20 vol.-% lithium metasilicate crystals. The term "main crystal phase" denotes the crystal phase which has the highest portion by volume compared with other crystal phases.

Figure 2:
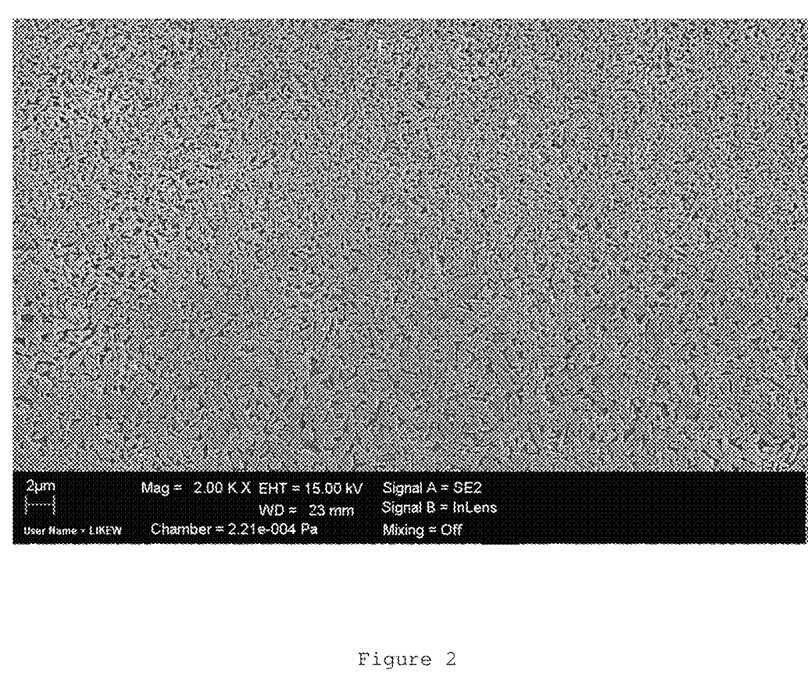
FIG. 2 shows an SEM image of a section through a block with precipitated lithium disilicate.
Figure 4:
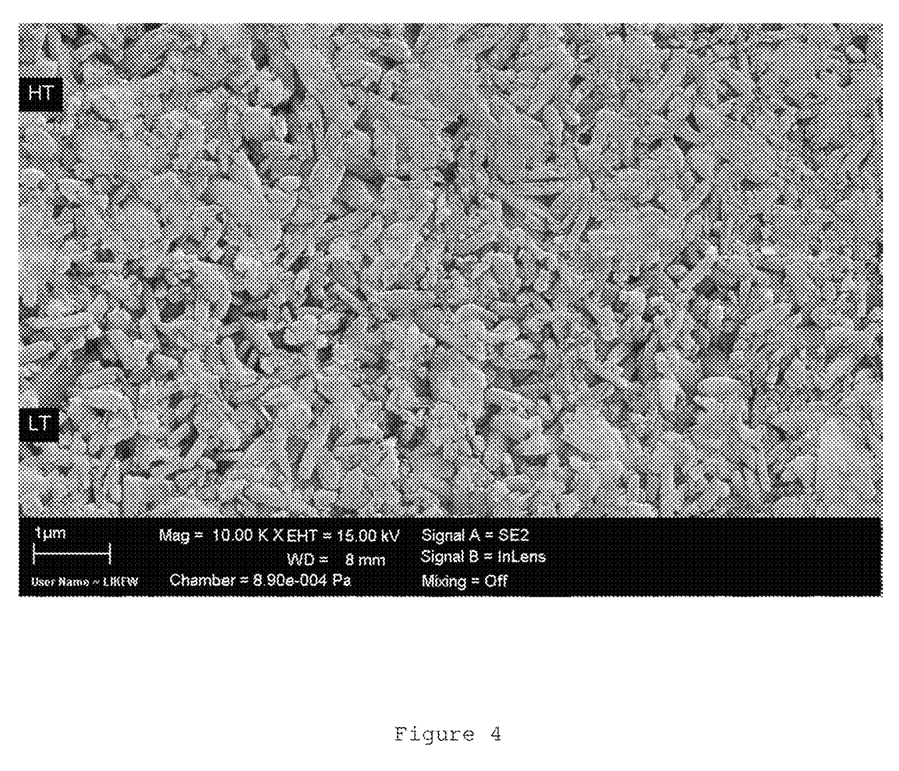
FIG. 4 shows an SEM image of a section through a block with lithium disilicate.
Figure 6:
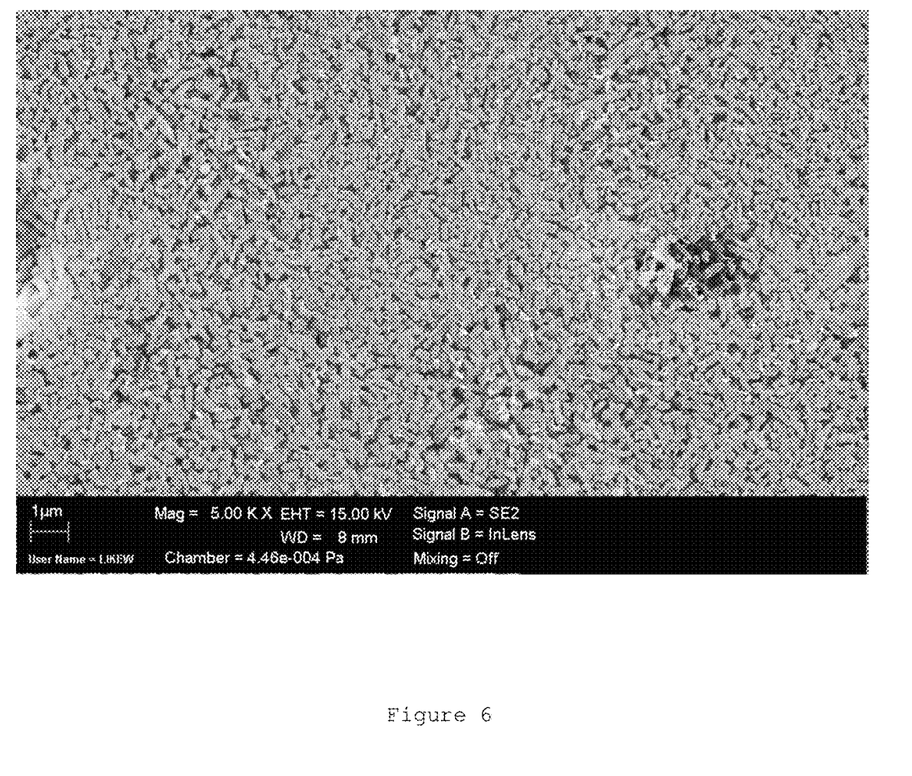
FIG. 6 shows an SEM image of a section through a block with lithium disilicate.

It has surprisingly become apparent that the blank according to the invention can not only be easily given the shape of the desired dental restoration by machining, but that it can also be converted to a high-strength dental restoration by heat treatment without substantial shrinkage. This heat treatment leads to the crystallization of high-strength lithium disilicate glass ceramic in the layers. It is particularly surprising that the crystallization of lithium disilicate takes place not only in the volume of the monolithic layers, but also across the boundary surface of the layers. This is shown by FIGS. 2, 4 and 6.

It is likewise possible to firstly convert the blank according to the invention with layers of lithium silicate glass, lithium silicate glass with nuclei or lithium metasilicate glass ceramic by heat treatment to a corresponding blank with layers of lithium disilicate glass ceramic. This blank with layers of lithium disilicate glass ceramic can then be processed in particular by machining to the desired dental restoration.

The invention therefore also relates to a blank for dental purposes which has at least 2 layers, bonded to one another, of
lithium disilicate glass ceramic,
wherein the layers differ in colour and the layers are monolithic.

It is preferred that the layers consist of lithium disilicate glass ceramic.

A blank is preferred in which the lithium disilicate glass ceramic comprises lithium disilicate as main crystal phase and in particular comprises more than 30 vol.-%, preferably more than 40 vol.-% and particularly preferably more than 50 vol.-% lithium disilicate crystals. The term "main crystal phase" denotes the crystal phase which has the highest portion by volume compared with other crystal phases.

Preferred embodiments for both the blank according to the invention with layers of lithium silicate glass, lithium silicate glass with nuclei or lithium metasilicate glass ceramic and the blank according to the invention with layers of lithium disilicate glass ceramic are described below.

Those blanks are preferred in which the lithium silicate glass, the lithium silicate glass with nuclei, the lithium metasilicate glass ceramic and the lithium disilicate glass ceramic comprises at least one and preferably all of the following components in the given amounts:

| Component | wt.-% |
|---|---|
| $SiO_2$ | 50.0 to 80.0 |
| $Li_2O$ | 6.0 to 20.0 |
| $Me(I)_2O$ | 0 to 10.0, in particular 0.1 to 10.0 |
| $Me(II)O$ | 0 to 12.0, in particular 0.1 to 12.0 |
| $Me(III)_2O_3$ | 0 to 8.0, in particular 0.1 to 8.0 |
| $Me(IV)O_2$ | 0 to 8.0, in particular 0.1 to 8.0 |
| $Me(V)_2O_5$ | 0 to 8.0, in particular 0.1 to 8.0 |
| $Me(VI)O_3$ | 0 to 8.0, in particular 0.1 to 8.0 |
| nucleating agent | 0 to 8.0, in particular 0.1 to 8.0, | wherein
$Me(I)_2O$ is selected from $Na_2O$, $K_2O$, $Rb_2O$, $Cs_2O$ or mixtures thereof,
$Me(II)O$ is selected from $CaO$, $BaO$, $MgO$, $SrO$, $ZnO$ and mixtures thereof,
$Me(III)_2O_3$ is selected from $Al_2O_3$, $La_2O_3$, $Bi_2O_3$, $Y_2O_3$, $Yb_2O_3$ and mixtures thereof,
$Me(IV)O_2$ is selected from $ZrO_2$, $TiO_2$, $SnO_2$, $GeO_2$ and mixtures thereof,
$Me(V)_2O_5$ is selected from $Ta_2O_5$, $Nb_2O_5$ and mixtures thereof,
$Me(VI)O_3$ is selected from $WO_3$, $MoO_3$ and mixtures thereof,
and nucleating agent is selected from $P_2O_5$, metals and mixtures thereof.

$Na_2O$ and $K_2O$ are preferred as oxides of monovalent elements $Me(I)_2O$.

$CaO$, $MgO$, $SrO$ and $ZnO$ are preferred as oxides of divalent elements $Me(II)O$.

$Al_2O_3$, $La_2O_3$ and $Y_2O_3$ are preferred as oxides of trivalent elements $Me(III)_2O_3$.

$ZrO_2$, $TiO_2$ and $GeO_2$ are preferred as oxides of tetravalent elements $Me(IV)O_2$.

$Ta_2O_5$ and $Nb_2O_5$ are preferred as oxides of pentavalent elements $Me(V)_2O_5$.

$WO_3$ and $MoO_3$ are preferred as oxides of hexavalent elements $Me(VI)O_3$.

$P_2O_5$ is preferred as nucleating agent.

The lithium silicate glass, the lithium silicate glass with nuclei, the lithium metasilicate glass ceramic and the lithium disilicate glass ceramic comprise $SiO_2$ and $Li_2O$ preferably in a molar ratio in the range of from 1.5 to 3.0, in particular 2.0 to 2.8 and preferably 2.20 to 2.45.

In a further preferred embodiment the lithium silicate glass, the lithium silicate glass with nuclei, the lithium metasilicate glass ceramic and the lithium disilicate glass ceramic comprise at least one and preferably all of the following components in the given amounts:

| Component | wt.-% |
|---|---|
| $SiO_2$ | 65.00 to 75.00 |
| $Li_2O$ | 14.00 to 16.00 |
| $K_2O$ | 2.00 to 5.00 |
| SrO and CaO | 0 to 2.00 |
| MgO | 0 to 2.00 |
| ZnO | 0 to 2.00 |
| $Al_2O_3$ | 1.50 to 3.50 |
| $La_2O_3$ | 0 to 2.00 |
| $ZrO_2$ | 0 to 4.00 |
| $P_2O_5$ | 2.50 to 4.00 |

It is further preferred that the lithium silicate glass, the lithium silicate glass with nuclei, the lithium metasilicate glass ceramic and the lithium disilicate glass ceramic comprise colorants and/or fluorescent agents.

Examples of colorants are oxides of d- and f-elements, such as the oxides of Ti, V, Sc, Mn, Fe, Co, Ta, W, Ce, Pr, Nd, Tb, Er, Dy, Gd, Eu and Yb. Metal colloids, e.g. of Ag, Au and Pd, can be used as colorants and in addition can also act as nucleating agents. These metal colloids can be formed e.g. by reduction of corresponding oxides, chlorides or nitrates during the melting and crystallization processes.

The blanks according to the invention are preferably present in the form of blocks, disks or cylinders. In these forms they can be particularly easily further processed to form the desired dental restorations.

In a further preferred embodiment, the blanks according to the invention have a holding means for fixing them in a processing device. The holding means allows the blanks to be secured in a processing device, such as in particular a milling or grinding device. The holding means is usually in the form of a pin and the holding means preferably consists of metal or plastic.

The invention likewise relates to a process for producing the blanks according to the invention.

The process for producing the blank according to the invention with monolithic layers of lithium silicate glass, lithium silicate glass with nuclei or lithium metasilicate glass ceramic is characterized in that
(i) monolithic layers of lithium silicate glass, lithium silicate glass with nuclei or lithium metasilicate glass ceramic are arranged on top of one another and
(ii) the layers are bonded to one another.

In a preferred embodiment of this process layers of lithium silicate glass or lithium silicate glass with nuclei are converted to layers of lithium silicate glass with nuclei or lithium metasilicate glass ceramic. This conversion is carried out in particular by at least one heat treatment. Preferred conditions for a conversion of lithium silicate glass to lithium silicate glass with nuclei and further to a corresponding lithium metasilicate glass ceramic and finally also to the corresponding lithium disilicate glass ceramic have already been described above.

Particularly preferably layers of lithium silicate glass or lithium silicate glass with nuclei are bonded to one another by at least one heat treatment and converted to layers of lithium metasilicate glass ceramic. The bonding and conversion can be carried out in one step and also in separate steps.

To produce the monolithic layers arranged on top of one another usually the lithium silicate glass is prepared first. For this purpose a mixture of suitable starting materials, such as carbonates, oxides, phosphates and fluorides, is melted for 2 to 10 h at temperatures of in particular 1300 to 1600° C. To achieve a particularly high homogeneity, the obtained glass melt is poured into water in order to form a granular glass material, and the obtained granular material is then melted again.

The obtained melt of the lithium silicate glass is then usually poured into a suitable mould in order to form a first monolithic layer. In the same way then generally a second monolithic layer of a different colour is produced from the melt of a further lithium silicate glass. This process can be repeated in order to produce yet further monolithic layers of different colours.

The obtained monolithic layers of lithium silicate glass can also be subjected to a heat treatment at in particular 500 to 600° C. in order to effect the formation of nuclei for the crystallization of lithium metasilicate and/or lithium disilicate. Monolithic layers of lithium silicate glass with nuclei are then present. The heat treatment is preferably carried out for a period of 10 to 180 min. Subsequent to the heat treatment it is preferred to cool the layers to room temperature in controlled manner. This effects in particular a stress-relief in the nucleated glass.

The obtained monolithic layers of lithium silicate glass with nuclei can then be subjected to a heat treatment at in particular 550 to 750° C. in order to effect the crystallization of lithium metasilicate. Monolithic layers of lithium metasilicate glass ceramic are then present. The heat treatment is preferably carried out for a period of 5 to 60 min.

In stage (i) of the process according to the invention the obtained monolithic layers of lithium silicate glass, lithium silicate glass with nuclei or lithium metasilicate glass ceramic are arranged on top of one another. This can be carried out e.g. simply by stacking the layers on top of one another.

The monolithic layers are bonded together in stage (ii). This can be carried out in particular by heat treatment or use of a bonding means.

In a first preferred embodiment of the process according to the invention
(a1) a monolithic layer is applied in the form of a melt to another monolithic layer.

In this way the layers are not only arranged on top of one another but are also bonded to one another.

It is preferred in this embodiment to use monolithic layers of lithium silicate glass.

It is further preferred that one monolithic layer in the form of a melt has a temperature of from 1100 to 1500° C. and the other monolithic layer has a temperature of from 400 to 600° C. The temperature difference between the layers helps to prevent the layers from becoming mixed and the occurrence of stresses in the blank.

In particular the procedure is such that the melt of a first lithium silicate glass is produced at in particular 1350 to 1500° C. and cast in a suitable mould to form a monolithic layer. This layer is cooled to a temperature of from 400 to 600° C. Then the melt of a second lithium silicate glass is poured onto this first layer in order to form a second, differently coloured, layer. In this procedure the layers fuse and are firmly bonded to one another.

By pouring on the melt of further lithium silicate glasses, blanks with more than two layers can also be obtained.

Using the above-described heat treatments the lithium silicate glass can be converted to lithium silicate glass with nuclei, lithium metasilicate glass ceramic and finally also to lithium disilicate glass ceramic in order to produce corresponding blanks.

In a second preferred embodiment of the process according to the invention (b1) the monolithic layers arranged on top of one another are heated to a temperature of at least 500° C. and in particular a temperature in the range of from 550 to 750° C.

Preferably layers of lithium silicate glass with nuclei are used.

A fusing at the boundary surface and thus a bonding of the layers takes place as a result of the action of heat. The heating is carried out in particular for a period of 5 to 60 min.

It is of particular advantage that as a result of the heating not only is a bonding between the layers achieved but the crystallization of lithium metasilicate can also be effected. To effect crystallization the layers are heated to in particular 550 to 750° C. It is likewise possible to firstly effect the joining of the layers at a gradually increasing temperature, starting from room temperature, and to then, at a temperature suitable for the formation of metasilicate, effect its crystallization.

Accordingly, with this embodiment, in particular blanks with layers of lithium metasilicate glass ceramic can also easily be produced.

It is particularly preferable to press the layers together during the heating at a pressure of in particular 0.01 to 4.0 MPa.

It is further preferred to smooth the surfaces facing one another of the layers. This can take place by customary grinding and polishing. In particular diamond disks and SiC paper can be used as grinding and polishing means.

With smooth surfaces there is generally at most a low pressing pressure of e.g. about 0.01 MPa, required in order to achieve an excellent joining of the glass layers. With non-smoothed surfaces generally pressing pressures of 1 to 4 MPa are applied.

The pressing pressure is applied to the stacked layers in particular via polished surfaces of $Si_3N_4$, steel, graphite, $Al_2O_3$ and/or $ZrO_2$. It is also possible to use a release agent such as BN in order to prevent the layers from sticking to the ram. The use of a ram with embossed relief is also possible.

The layers used can in particular be layers cast in suitable dimensions or even large plates or rods from which layers with suitable dimensions were cut.

In a third preferred embodiment of the process according to the invention (c1) a bonding means is provided between the monolithic layers.

In particular a glass solder, a crystallizing glass solder, a glass ceramic solder or an adhesive come into consideration as bonding means.

There come into consideration as glass solder, crystallizing glass solder and glass ceramic solder in particular glasses and glass ceramics which melt at low temperature and in particular a temperature of from 550 to 750° C. They are usually applied as powders, slips or pastes to the layers to be bonded. The solder melts as a result of temperature treatment and coats the surfaces of the layers. After cooling, in this way a solid bond provided via the solder forms between the layers. It is preferred to heat the monolithic layers provided with the solder and arranged on top of one another at least to the melt temperature of the solder.

By heating the solder the crystallization of lithium metasilicate in the layers can also take place simultaneously. To effect this crystallization, heating to in particular 550 to 750° C. takes place. It is likewise possible to firstly effect the melting of the solder and thus the bonding of the layers at a gradually increasing temperature, starting from room temperature, and to then, at a temperature suitable for the formation of lithium metasilicate, effect its crystallization.

In particular polymerizable adhesives with glass as filler come into consideration as adhesives. Those glass fillers are preferred which crystallize upon heat treatment. Those glasses which have a composition like that of the glass of one of the layers to be bonded or like that of a mixture of the glasses of the layers to be bonded are particularly preferred as fillers.

The adhesives are applied, e.g. by spreading, to at least one of the layers to be bonded. The layers are arranged on top of one another and the adhesive is then cured in customary manner. In this way a blank of bonded layers is obtained which can be further processed to form a dental restoration.

It is preferred to bond layers of lithium silicate glass, lithium silicate glass with nuclei and lithium metasilicate glass ceramic with the adhesive.

The blanks with layers of lithium silicate glass, lithium silicate glass with nuclei or lithium metasilicate glass ceramic produced with the process according to the invention can be easily converted to a blank with layers of lithium disilicate glass ceramic. The convertibility of the precursors lithium silicate glass, lithium silicate glass with nuclei and lithium metasilicate glass ceramic to lithium disilicate glass ceramic has already been described above.

The process for producing the blank according to the invention with layers of lithium disilicate glass ceramic is characterized in that (iii) the blank according to the invention with layers of lithium silicate glass, lithium silicate glass with nuclei and lithium metasilicate glass ceramic is subjected to at least one heat treatment in order to convert the lithium silicate glass, the lithium silicate glass with nuclei or the lithium metasilicate glass ceramic to lithium disilicate glass ceramic.

Preferably a blank with layers of lithium silicate glass with nuclei or with layers of lithium metasilicate glass ceramic is subjected to the heat treatment.

The heat treatment is preferably carried out at a temperature of at least 750° C. and in particular a temperature in the range of from 750 to 950° C.

Because of their properties the blanks according to the invention are particularly suitable for being further processed to form dental restorations.

The invention therefore also relates to a process for producing dental restorations, in which (d1) the blank according to the invention with layers of lithium silicate glass, lithium silicate glass with nuclei or lithium metasilicate glass ceramic is given the shape of the dental restoration by machining, (d2) at least one heat treatment is carried out in order to convert the lithium silicate glass, the lithium silicate glass with nuclei or the lithium metasilicate glass ceramic to lithium disilicate glass ceramic, and (d3) optionally the surface of the obtained dental restoration is provided with a finish.

or in an alternative embodiment (e1) the blank according to the invention with layers of lithium disilicate glass ceramic is given the shape of the dental restoration by machining and (e2) optionally the surface of the obtained dental restoration is provided with a finish.

The dental restorations, shaped as desired, can be easily machined from the blanks according to the invention. For this purpose, in particular blanks with layers of lithium silicate glass with nuclei (d1), lithium metasilicate glass ceramic (d1) or lithium disilicate glass ceramic (e1) are used.

The machining in stages (d1) and (e1) is usually carried out by material removal processes and in particular by milling and/or grinding. It is preferred that the machining is carried out with computer-controlled milling and/or grinding devices. Particularly preferably the machining is carried out as part of a CAD/CAM process.

In stage (d2) the blank is subjected to a heat treatment in order to effect the controlled crystallization of lithium disilicate and thus the formation of lithium disilicate glass ceramic. The heat treatment takes place in particular at a temperature of from 750 to 950° C. and preferably 800 to 900° C. The heat treatment is carried out in particular for a period of from 1 to 30 min, preferably 2 to 15 min.

The heat treatment can also serve to burn off adhesive which was used during production of the blank used. However, it is also possible to burn off adhesive as a separate step before the crystallization of lithium disilicate in stage (d2).

It is particularly surprising that in particular the crystallization of lithium disilicate also takes place across the interface of the layers, as could be established by scanning electron microscope examinations (SEM examinations). It is assumed that this phenomenon contributes substantially to the secure bonding of the layers and effectively counteracts a weakening of the obtained dental restoration at this interface.

After stages (d2) and (e1) have been carried out, dental restorations are obtained with layers of lithium disilicate glass ceramic, which have excellent mechanical properties and a high chemical stability. Additionally, because of the several layers of different colour, they afford an excellent imitation of the optical properties of natural tooth material, e.g. of dentine to incisal colour transitions. Finally, the restorations can also be produced from the blanks according to the invention without substantial shrinkage. This is due in particular to the fact that the blanks according to the invention have monolithic layers and not discontinuous layers such as layers of powder or granular material. Such discontinuous layers also have to be densely-sintered to give the final restoration, which is accompanied by a significant shrinkage. Through use of the blanks according to the invention, therefore, dental restorations with precisely the desired dimensions can easily be produced.

The dental restorations produced according to the invention are preferably selected from crowns, abutments, abutment crowns, inlays, onlays, veneers, shells and bridges as well as overstructures for multi-part restoration frameworks which can consist e.g. of oxide ceramic, metals or dental alloys.

In the optional stages (d3) and (e2), the surface of the dental restoration can also be provided with a finish. It is possible in particular to also carry out a glazing firing at a temperature of from 700 to 850° C. or to polish the restoration. Additionally a layering material of glasses and/or glass ceramics can also be applied.

A finishing with a glaze and the crystallization of lithium disilicate can naturally also be carried out in one step.

Because of the described special properties of the blanks according to the invention, they are suitable in particular for producing dental restorations. The invention therefore also relates to the use of the blanks for producing dental restorations and in particular crowns, abutments, abutment crowns, inlays, onlays, veneers, shells and bridges as well as over structures.

The invention is explained in more detail below by means of examples.

EXAMPLES

The examples explain in particular the production of two-layer blanks. In analogous manner blanks with more than 2 and up to 10 layers of different colours can be produced. The sequence of layers was chosen such that the transition of colour, opalescence and translucence of natural tooth material was imitated as naturally as possible.

Example 1—Fusion Casting Process

This example describes the production of a blank according to the invention in the shape of a block with 2 differently coloured monolithic layers of lithium silicate glass, the nucleation in the glass and its conversion to lithium metasilicate glass ceramic as well as the processing of the block with layers of lithium metasilicate glass ceramic to form a highly aesthetic dental restoration made of lithium disilicate glass ceramic.

Two lithium silicate glasses with the following composition were melted.
Glass 1:
  Composition in wt.-%:
  74.36 $SiO_2$, 3.26 $K_2O$, 15.45 $Li_2O$, 3.55 $Al_2O_3$, 3.38 $P_2O_5$
Glass 2:
  Composition in wt.-%:
  70.64 $SiO_2$, 3.09 $K_2O$, 14.68 $Li_2O$, 3.38 $Al_2O_3$, 3.21 $P_2O_5$, 3.00 $ZrO_2$, 2.00 colouring oxides Firstly, the glasses were melted at 1450 to 1500° C. from suitable starting substances. After sufficient homogenization, the melt from glass 1 was poured into a graphite mould to form a monolithic layer and the layer was cooled to 500 to 550° C. within 30 to 60 seconds. Then, the melt of glass 2 was poured into the graphite mould onto the cooled glass layer. In this way a homogeneous fusing of the glass layers was effected without additional pressing pressure. Further glass layers could be poured on analogously to the described process.

The at least two-layer glass block removed from the mould was subjected to a heat treatment in a furnace at 500° C. for 10 min in order to carry out the nucleation, and cooled to room temperature in controlled manner.

Then the block was subjected to a heat treatment at 650° C. for 20 min in order to effect the controlled crystallization of lithium metasilicate in the layers. A block with layers of lithium metasilicate glass ceramic was obtained.

Figure 1:
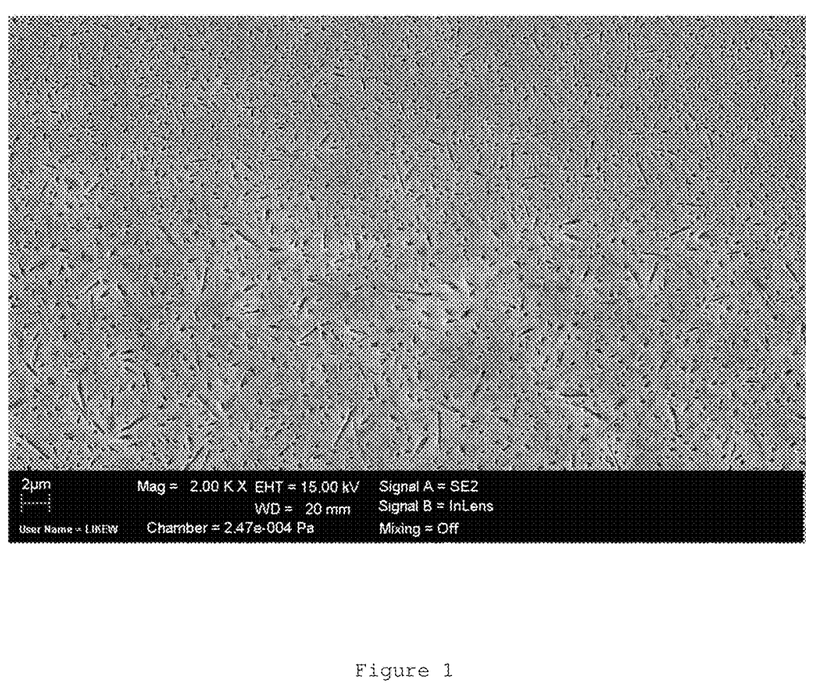
FIG. 1 shows an SEM image of a section through a block with lithium metasilicate.

The SEM image of a section through the block with lithium metasilicate is shown in FIG. 1, after the surface had been treated for 8 s with aqueous HF solution in order to slightly etch the crystal phase and make the structure visible. The excellent joining of the layers at the boundary surface and the crystallization across the boundary surface is shown.

This block was able to be given the shape of dental restorations by means of CAD/CAM processes. Lithium disilicate was precipitated by the subsequent heat treatment at 850° C. for 10 min and thus the desired high-strength dental restoration was obtained which, because of its several layers of different colour, had an appearance like that of a natural tooth.

The SEM image of a section through a block with precipitated lithium disilicate is shown in FIG. 2, after the surface had been treated for 30 s with HF vapour to slightly etch the crystal phase and make the structure visible. A very homogeneous structure can surprisingly be seen across the boundary surface, which causes the boundary surface to disappear almost completely. The preparation from several different glass layers is only recognizable from the different colour of these layers.

Example 2—Joining Glass Layers Using Temperature and Pressure 2 to 10 glass layers were shaped into monolithic blanks in a hot joining process at 500 to 750° C. under the action of a pressure of 0.01 to 4 MPa. As a result of this heat treatment it was possible to allow not only the joining of the different glass layers to take place but also their crystallization.

Example 2A—Ground Surfaces, Low Pressure—0.01 MPa (a) Preparing Glass Layers with Nuclei Firstly, two lithium silicate glasses with the following composition were melted at 1450 to 1500° C.
Glass 3:
Composition in wt.-%:
70.68 $SiO_2$, 4.00 $K_2O$, 14.68 $Li_2O$, 3.38 $Al_2O_3$, 3.21 $P_2O_5$, 0.26 MgO, 0.85 $ZrO_2$, 2.94 colouring oxides
Glass 4:
Composition in wt.-%:
70.99 $SiO_2$, 4.74 $K_2O$, 14.76 $Li_2O$, 1.49 $Al_2O_3$, 3.28 $P_2O_5$, 0.70 ZnO, 0.99 $ZrO_2$, 3.05 colouring oxides The obtained melts were then poured into moulds to form glass layers with the desired dimensions.

The glass layers were heat-treated for 10 min at 500° C. in order to form nuclei. They were then cooled to room temperature in controlled manner.

The surfaces of the glass layers to be bonded were then ground and polished exactly plane-parallel. For this purpose, they were firstly ground plane-parallel with a 74-μm diamond disk and then treated in a first polishing step with a 20-μm diamond disk and then in a second polishing step with 1000-grit SiC paper. The obtained surfaces were cleaned with water and optionally also ethanol or acetone.

(b) Bonding the Glass Layers and Crystallization of Lithium Metasilicate

The two glass layers were laid precisely on top of one another and pressed together at a pressure of 0.01 MPa by the action of force perpendicular to the surfaces to be joined. The glass layers pressed together were then heated, starting at 400° C., to 650° C. within 25 min in order to achieve the joining of the layers. By maintaining a temperature of approximately 650 to 660° C. for 20 min the crystallization of lithium metasilicate was then triggered. The obtained crystallized block was then cooled to room temperature in controlled manner.

Figure 3:
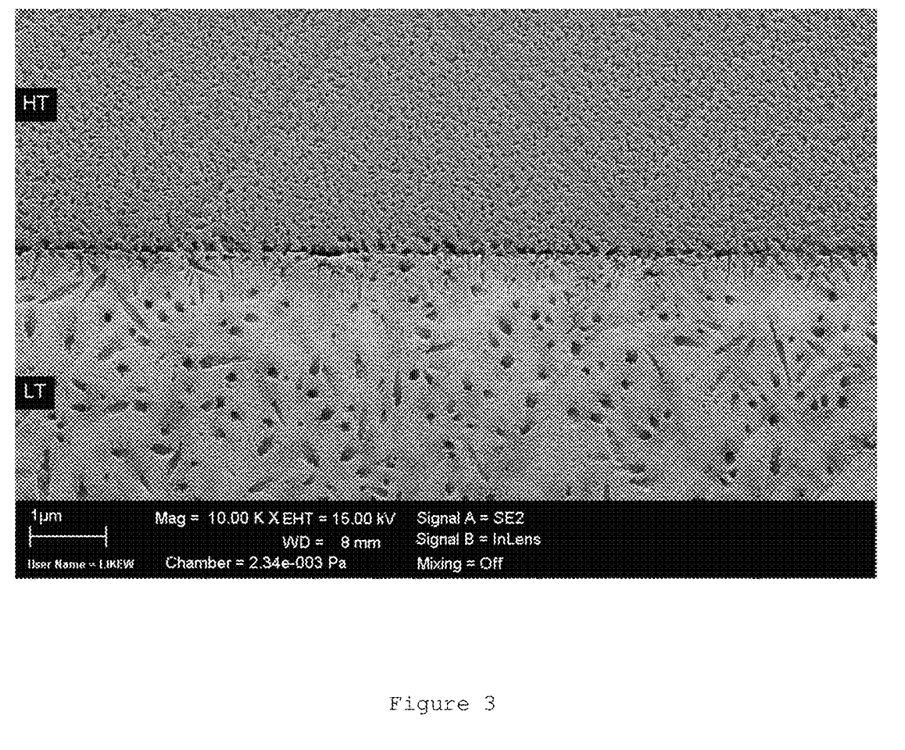
FIG. 3 shows an SEM image of a section through a block with lithium metasilicate.

The SEM image of a section through the block with lithium metasilicate is shown in FIG. 3, after the surface had been treated for 8 s with aqueous HF solution to slightly etch the crystal phase and thus make the structure visible. This image also showed a very good joining of the layers as well as the start of a crystallization across the boundary surface.

(c) Machining and Lithium Disilicate Crystallization

The obtained block with different layers of lithium metasilicate glass ceramic could be machined easily with customary CAM units, such as Cerec MC XL, from Sirona, in order to give it the shape of the desired dental restorations.

After machining the lithium metasilicate glass ceramic was converted to lithium disilicate glass ceramic by heat treatment for 10 min at 850° C. A dental restoration with the sought final strength was thereby achieved. Additionally it had a very attractive appearance in the form of a colour gradation which corresponded to the dentine to incisal colour transition.

The SEM image of a section through a block with lithium disilicate, which has not been subjected to machining, is shown in FIG. 4, after the surface had been treated for 30 s with HF vapour. Here too a very homogeneous structure can also surprisingly be seen across the interface, which causes the interface to disappear almost completely. The preparation from several different glass layers is recognizable only from the different colour of these layers.

Example 2B—Unground Surfaces, High Pressure—1.5 MPa

Example 2A was repeated. However, the surfaces of the glass layers were not ground and they were joined together at a higher pressure of 1.5 MPa and by a modified heat treatment and crystallized to form lithium metasilicate glass ceramic.

During this heat treatment the glass layers pressed together were heated, starting at 550° C., to 680° C. within 2 min in order to achieve the joining of the layers. By maintaining a temperature of about 680° C. for about 20 min the crystallization of lithium metasilicate was then triggered. The obtained crystallized block was subsequently cooled to room temperature in controlled manner.

Figure 5:
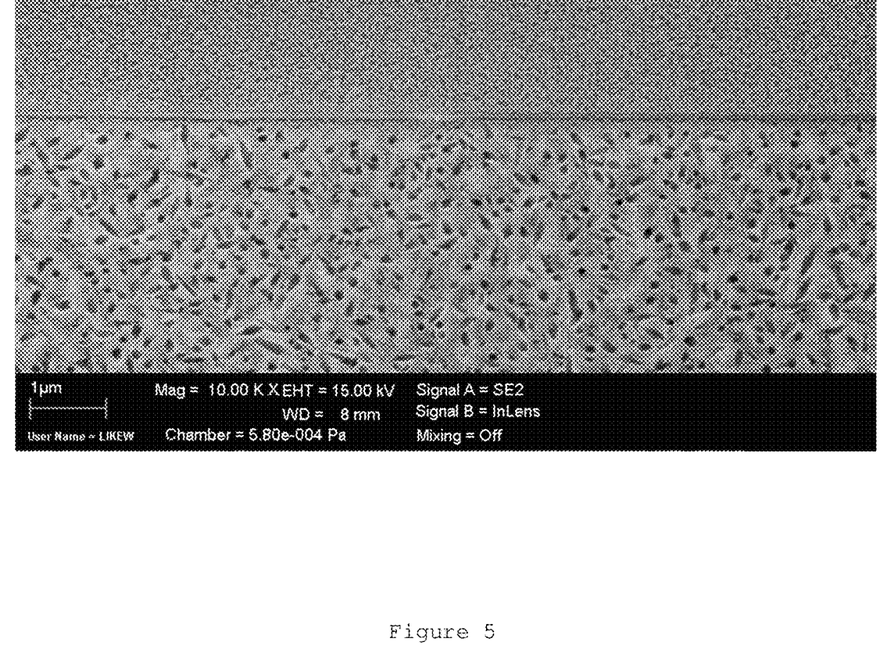
FIG. 5 shows an SEM image of a section through a block with lithium metasilicate.

The SEM image of a section through the block with lithium metasilicate is shown in FIG. 5, after the surface had been treated for 8 s with aqueous HF solution. This image also showed a very good joining of the layers.

After machining the lithium metasilicate glass ceramic was converted to lithium disilicate glass ceramic by heat treatment for 10 min at 850° C. A dental restoration with the desired final strength was thereby achieved. Additionally it had a very attractive appearance in the form of a colour gradation which corresponded to the dentine to incisal colour transition.

The SEM image of a section through a block with lithium disilicate, which has not been machined, is shown in FIG. 6, after the surface had been treated for 30 s with HF vapour. Here too a very homogeneous structure can surprisingly be seen across the boundary surface, which causes the boundary surface to disappear almost completely. The preparation from several different glass layers is likewise recognizable only from the different colour of these layers.

Example 3—Joining Glass Layers by Means of Solder

In an analogous manner to Example 2 A, different layers of glass with nuclei were prepared from glass 3 and glass 4.

A powdered sintering glass solder with an average pore size $D_{50}$ of 6 to 10 μm, relative to the number of particles, is applied to the surfaces to be joined of the two different glass layers with nuclei, and the coated surfaces were laid precisely on top of one another.

The glass layers were then subjected to a controlled, multi-step heat treatment. The glass layers were heated from room temperature at a rate of 10 K/min to 700° C., held at this temperature for 10 min and then cooled down to room temperature again at a rate of about 20 K/min. A vacuum of about 50 mbar was applied from about 550° C. until the end of the holding time. The sinter-active glass solder melted as a result of the heat treatment and, by coating the glass surfaces, bonded them. Likewise lithium metasilicate crystals formed in the volume of the glass layers during the heat treatment. The obtained block with layers of lithium metasilicate glass ceramic was then cooled in controlled manner.

The block could easily be given the shape of dental restorations by machining with customary CAM units, such as Cerec® MC XL from Sirona.

After the machining the lithium metasilicate glass ceramic was converted to lithium disilicate glass ceramic by heat treatment for 10 min at 850° C. A dental restoration with the sought final strength was thereby achieved. Additionally it had a very attractive appearance in the form of a colour gradation which corresponded to the dentine to incisal colour transition.

Example 4—Joining Glass Layers by Means of Adhesive

Firstly, in an analogous manner to Example 2 A, different glass layers with nuclei were prepared from glass 3 and glass 4.

These glass layers were then subjected to a controlled, multi-step heat treatment. The glass layers were heat-treated for 10 min at 500° C. in order to form nuclei for lithium metasilicate. Then a further heat treatment was carried out at 650° C. which led to the formation of lithium metasilicate as main crystal phase in the volume of the glass layers. The obtained layers of lithium metasilicate glass ceramic were then cooled in controlled manner.

The following composite adhesive with crystallizing glass filler was spread onto the surfaces to be bonded of the glass ceramic layers and the layers were laid precisely on top of one another.

Dual-curing composite adhesive with crystallizing glass filler component:

Composite with 60 wt.-% crystallizing glass filler ($d_{50}<10$ μm, preferably $d_{50}=7$ μm)

Composition of the composite in wt.-%

| | |
|---|---|
| Urethane acrylate oligomer | 15-25 |
| Isobornyl acrylate | 40-50 |
| N,N-dimethacrylamide | 15-25 |
| Adhesion promoter | 1-5 |

Composition of crystallizing glass filler in wt.-%:
70.82 $SiO_2$, 4.37 $K_2O$, 14.72 $Li_2O$, 2.44 $Al_2O_3$, 3.25 $P_2O_5$, 0.13 MgO, 0.35 ZnO, 0.92 $ZrO_2$, 3.00 colouring oxides After the adhesive had cured, a block with two layers of lithium metasilicate glass ceramic had formed which could be machined analogously to Example 3 and converted by crystallization of lithium disilicate to a high-strength and optically very attractive dental restoration. The composite was completely thermally decomposed during the heat treatment used for the crystallization of lithium disilicate and the glass ceramic layers bonded together. The crystallizing glass filler also acted as sintering glass solder.

Example 5

Analogously to Examples 1 to 4 further multilayer blanks were produced and processed to form dental restorations by means of CAD/CAM processes. The glasses listed in Table 1 below were used. With their help, an excellent joining of the monolithic layers and a very good colour gradation of the layers could likewise be achieved.

TABLE 1

| Component | Glass 5 wt.-% | Glass 6 wt.-% | Glass 7 wt.-% | Glass 8 wt.-% | Glass 9 wt.-% | Glass 10 wt.-% | Glass 11 wt.-% |
|---|---|---|---|---|---|---|---|
| $SiO_2$ | 71.52 | 71.39 | 72.09 | 71.02 | 69.20 | 69.76 | 71.16 |
| $K_2O$ | 4.21 | 4.20 | 4.24 | 4.29 | 3.80 | 3.70 | 4.19 |
| SrO | 0.00 | 1.00 | 0.00 | 0.99 | 0.00 | 0.00 | 0.00 |
| $Li_2O$ | 14.89 | 14.86 | 15.01 | 14.78 | 15.10 | 15.00 | 14.81 |
| $Al_2O_3$ | 3.31 | 1.17 | 3.33 | 1.16 | 3.40 | 2.00 | 3.29 |
| $P_2O_5$ | 3.27 | 3.28 | 3.30 | 3.27 | 3.30 | 3.50 | 3.25 |
| MgO | 1.00 | 0.00 | 1.01 | 0.00 | 0.00 | 0.00 | 1.00 |
| $ZrO_2$ | 0.80 | 2.00 | 0.00 | 1.99 | 0.60 | 2.00 | 0.00 |
| ZnO | 0.00 | 1.00 | 0.00 | 1.40 | 2.00 | 2.00 | 0.00 |
| $CeO_2$ | 0.50 | 0.60 | 0.51 | 0.60 | 1.70 | 0.60 | 1.70 |
| $La_2O_3$ | 0.00 | 0.00 | 0.00 | 0.00 | 0.30 | 1.00 | 0.00 |
| $V_2O_5$ | 0.00 | 0.00 | 0.00 | 0.00 | 0.10 | 0.04 | 0.10 |
| $Tb_4O_7$ | 0.50 | 0.50 | 0.51 | 0.50 | 0.50 | 0.40 | 0.50 |

Selected properties of these glasses and the glass ceramics produced from them are listed in Table 2 below.

TABLE 2

| | Glass 5 | Glass 6 | Glass 7 | Glass 8 | Glass 9 | Glass 10 | Glass 11 |
|---|---|---|---|---|---|---|---|
| Colour values | | | | | | | |
| L* | 93.21 | 92.74 | 93.8 | 92.29 | 82.33 | 89.95 | 82.97 |
| a* | −0.49 | −0.78 | −0.54 | −0.71 | 3.27 | −1.48 | 2.21 |
| b* | 5.77 | 5.84 | 4.08 | 6.56 | 20.67 | 12.07 | 20.79 |
| CR value | 76.08 | 58.01 | 80.30 | 56.41 | 80.70 | 50.71 | 82.96 |
| DSC evaluation | | | | | | | |
| Tg [° C.] | 461.3 | 473.8 | 458.6 | 466 | 462 | 473.1 | 459.6 |
| E1 [° C.] | 654 | 668.9 | 646 | 669.9 | 637.5 | 648.1 | 644.7 |
| E2 [° C.] | 831 | 810 | 833 | 810 | 828 | 824.5 | 832.5 |
| Ts [° C.] | 962.7 | 971.3 | 968.9 | 971.2 | 958.9 | 969.5 | 962.8 |

TABLE 2-continued

|  | Glass 5 | Glass 6 | Glass 7 | Glass 8 | Glass 9 | Glass 10 | Glass 11 |
|---|---|---|---|---|---|---|---|
| CTE [$10^{-6} \cdot K^{-1}$] | | | | | | | |
| 100-500° C. | 10.47 | 10.5 | 10.58 | 10.42 | 10.45 | 10.37 | 10.39 |
| 100-600° C. | 10.9 | 11.19 | 11.07 | 11.08 | 10.85 | 10.65 | 11.05 |
| Molar ratio | | | | | | | |
| $SiO_2/Li_2O$ | 2.390 | 2.390 | 2.390 | 2.390 | 2.280 | 2.314 | 2.390 |
| Crystal phase portion | | | | | | | |
| 680° C./LS | 32% | 31% | 42% | 34% | 43% | 46% | 41% |
| 850° C./LS2 | 68% | 68% | 69% | 68% | 66% | 66% | 68% |
| Strength | | | | | | | |
| MPa | 500 | 505 | 517 | 509 | 461 | 460 | 595 |

Colour Values:

The colour values were determined using 2 mm-thick samples of the crystallized glass ceramics with a colour measuring device (Minolta CM3700D). The measured L*, a* and b* values show that the glass ceramics can be coloured in typical dentine colours. The CR value (contrast ratio) is a measure of the translucence. The achieved contrast values between 50% and 83% demonstrate that a gradation from incisal (high translucence) to dentine (less translucence) is possible without problems.

DSC Evaluation:

Characteristic temperatures of the glasses are given. Tg denotes glass transition. E1 stands for a $1^{st}$ exothermic reaction which correlates with the crystallization of the lithium metasilicate phase. E2 stands for a $2^{nd}$ exothermic reaction which correlates with the crystallization of the lithium disilicate phase. Is stands for the melting temperature of the lithium disilicate phase.

It has been shown that it is advantageous for a good bond between the joined glasses and glass ceramics if these temperatures differ only slightly from one another with the glasses and glass ceramics used, as is e.g. the case with glasses 5 to 11.

Coefficient of Thermal Expansion (CTE):

The CTE describes the thermal expansion behaviour of the glass ceramics. It is advantageous, for a stress-free bond of the glass ceramics, if the glass ceramics joined to one another have similar expansion coefficients.

Molar Ratio:

The molar ratio of $SiO_2$ to $Li_2O$ affects the proportions of the crystal phases formed.

Crystal Phase Portion:

The crystal phase portion of lithium metasilicate (LS) substantially determines the processability of the blank. The crystal phase portion of lithium disilicate (LS2) is of significant importance for the properties of the finished restoration.

Strength:

The strength was determined using "biaxial bending test specimens" from the respective lithium disilicate glass ceramic according to ISO 6872:2008.

Example 6

The glasses listed in Table 3 below were likewise processed, analogously to Examples 1 to 4, to form multilayer blanks and finally to form dental restorations.

TABLE 3

| Component | Glass 12 wt.-% | Glass 13 wt.-% | Glass 14 wt.-% | Glass 15 wt.-% | Glass 16 wt.-% | Glass 17 wt.-% | Glass 18 wt.-% | Glass 19 wt.-% | Glass 20 wt.-% | Glass 21 wt.-% | Glass 22 wt.-% | Glass 23 wt.-% | Glass 24 wt.-% |
|---|---|---|---|---|---|---|---|---|---|---|---|---|---|
| $SiO_2$ | 63.80 | 63.80 | 64.93 | 71.00 | 59.00 | 64.93 | 71.00 | 64.96 | 67.62 | 70.18 | 67.65 | 68.60 | 71.01 |
| $Li_2O$ | 13.60 | 13.60 | 13.45 | 14.81 | 12.40 | 13.45 | 14.81 | 13.49 | 14.94 | 15.47 | 14.00 | 15.12 | 14.74 |
| $P_2O_5$ | 3.00 | 3.00 | 3.00 | 2.50 | 3.90 | 3.00 | 2.50 | 2.95 | 3.8 | 3.80 | 3.90 | 4.36 | 3.09 |
| $Na_2O$ | | | | | | | | | 0.69 | | | | 0.20 |
| $K_2O$ | 3.00 | 3.00 | 3.00 | 4.20 | 3.50 | 3.00 | 4.20 | 3.51 | 1.08 | 4.46 | 3.90 | 3.86 | 3.95 |
| MgO | | | | | | | | | 0.3 | 5.00 | | 0.80 | |
| CaO | | | | | 0.50 | 1.00 | | | | | | | 0.45 |
| SrO | | | | | | | | | | | 7.00 | | |
| ZnO | | | | | | | | | 0.99 | | | 4.39 | |
| $B_2O_3$ | | | | | | | | | | | | | 0.10 |
| $Al_2O_3$ | 3.00 | 3.00 | 3.00 | 3.29 | 2.50 | 2.00 | 3.29 | 3.09 | 4.86 | 1.09 | 1.45 | 1.08 | 3.40 |
| $Y_2O_3$ | | | | | | | | 7.60 | | | | | |
| $La_2O_3$ | | | | | | | | | | | | 0.30 | |
| $Bi_2O_3$ | | | | | | | 3.20 | | | | | | |
| $TiO_2$ | | | | | 0.30 | | | | | | | | |
| $ZrO_2$ | 9.60 | 9.60 | 4.00 | | 5.00 | 8.00 | | 2.00 | 1.19 | | | | 0.64 |
| $GeO_2$ | | | | | 7.90 | | | | | | | | |
| $Ta_2O_5$ | | | 6.00 | 3.20 | 1.00 | 2.00 | | | 2.91 | | | | |
| $MoO_3$ | 4.00 | | | | | | | | | | | | |
| $WO_3$ | | 4.00 | | | | | | | | | | | |
| $V_2O_5$ | | | 0.12 | | | 0.12 | | 0.10 | 0.14 | | 0.10 | | 0.03 |
| $MnO_2$ | | | | | | | | | | | | | 0.04 |
| $Fe_2O_3$ | | | | | | | | | | | | 0.20 | 0.22 |
| $CeO_2$ | | | 1.90 | 0.50 | 1.80 | 1.90 | 0.50 | 1.80 | 1.38 | | 1.80 | 0.99 | 1.93 |

TABLE 3-continued

| Component | Glass 12 wt.-% | Glass 13 wt.-% | Glass 14 wt.-% | Glass 15 wt.-% | Glass 16 wt.-% | Glass 17 wt.-% | Glass 18 wt.-% | Glass 19 wt.-% | Glass 20 wt.-% | Glass 21 wt.-% | Glass 22 wt.-% | Glass 23 wt.-% | Glass 24 wt.-% |
|---|---|---|---|---|---|---|---|---|---|---|---|---|---|
| $Pr_2O_3$ | | | | | | 0.70 | | | | | | | |
| $Sm_2O_3$ | | | | | | 1.00 | | | | | | | |
| $Tb_4O_7$ | | | 0.50 | 0.50 | | 0.50 | 0.50 | 0.50 | 0.50 | 0.1 | | 0.50 | |
| $Er_2O_3$ | | | 0.10 | | | 0.10 | | | | | | | 0.19 |

Selected properties of these glasses and the glass ceramics produced from them are listed in Table 4 below. These properties were determined analogously to Example 5.

TABLE 4

| | Glass 12 | Glass 13 | Glass 14 | Glass 15 | Glass 16 | Glass 17 | Glass 18 | Glass 19 | Glass 20 | Glass 21 | Glass 22 | Glass 23 | Glass 24 |
|---|---|---|---|---|---|---|---|---|---|---|---|---|---|
| Colour | | | | | | | | | | | | | |
| L* | | | 76.03 | | | 79.65 | | 83.09 | 75.91 | 87.3 | | | 80.65 |
| a* | | | 6.22 | | | 3.71 | | 0.8 | 6.7 | 0.2 | | | 4.47 |
| b* | | | 32.1 | | | 27.27 | | 21.95 | 27.04 | 3.4 | | | 25.11 |
| CR | | | 51.92 | | | 64.83 | | 59.76 | 75.86 | 85 | | | 77.19 |
| DSC evaluation | | | | | | | | | | | | | |
| Tg [° C.] | 508 | 509 | 493 | 469 | 489 | 496 | 458 | 503 | | 460 | | | |
| E1 [° C.] | 649 | 651 | 652 | | 602 | 694 | | | | 610 | | | |
| E1 [° C.] | 820 | 819 | 807 | 711 | 792 | 850 | 671 | 753 | | 752 | | | |
| Ts [° C.] | 936 | 935 | 947 | 972 | 927 | 945 | 974 | 930 | | 965 | | | |
| CTE [$10^{-6} \cdot K^{-1}$] | | | | | | | | | | | | | |
| 100-500° C. | | | | | | 10.26 | | | 9.35 | | | | |
| 100-600° C. | | | | | | 10.74 | | | 9.92 | | | | |
| Molar ratio | | | | | | | | | | | | | |
| $SiO_2/Li_2O$ | 2.333 | 2.333 | 2.400 | 2.384 | 2.366 | 2.400 | 2.384 | 2.394 | 2.251 | 2.256 | 2.403 | 2.256 | 2.395 |
| Crystal phases | | | | | | | | | | | | | |
| 680° C. | | | LS | | LS | LS | LS2 | | LS | | | | LS |
| 850° C. | LS2 LP | LS2 LP | LS2 SiO$_2$ | LS2 | LS2 | LS2 | LS2 | LS2, LS | LS2 | LS2, LS | | | LS2 |
| Strength | | | | | | | | | | | | | |
| MPa | | | | | 419 | 352 | | | | 320 | 520 | | 478 |

LS—lithium metasilicate
LS2—lithium disilicate
LP—lithium phosphate

With glass 15, no lithium metasilicate (LS) crystallized, but crystallization of lithium disilicate (LS2) already took place at a temperature of 711° C. The machining therefore conveniently already took place after nucleation (500° C./10 min).

Like glass 15, glass 18 likewise did not form any LS. Crystallization of LS2 already took place at 670° C.

After the first crystallization, glass 19 showed only a small amount of lithium metasilicate crystal phase. The lithium disilicate glass ceramic present after the second crystallization had a very high translucence.

Example 7

A glass of the following composition was used as sintered glass solder analogously to Example 3 in order to bond together layers of nucleated glasses according to Table 1 at 690° C.

| Component | wt.-% |
|---|---|
| $SiO_2$ | 64.65 |
| $K_2O$ | 7.29 |
| $Na_2O$ | 6.75 |
| SrO | 2.22 |
| $Li_2O$ | 2.07 |
| CaO | 1.29 |
| $Al_2O_3$ | 6.61 |
| $B_2O_3$ | 1.71 |
| $TiO_2$ | 1.45 |
| $ZrO_2$ | 0.60 |
| ZnO | 3.08 |
| $CeO_2$ | 0.56 |
| F | 1.72 |

The invention claimed is:
1. Blank for dental purposes which has at least 2 layers, bonded to one another, of
lithium silicate glass,
lithium silicate glass with nuclei or
lithium metasilicate glass ceramic, wherein the layers differ in colour and the layers are monolithic.

2. Blank according to claim 1 which has layers of lithium silicate glass with nuclei or layers of lithium metasilicate glass ceramic.

3. Blank according to claim 1, in which the lithium metasilicate glass ceramic comprises lithium metasilicate as main crystal phase and comprises more than 5 vol.-% lithium metasilicate crystals.

4. Blank according to claim 3, in which the lithium metasilicate glass ceramic comprises lithium metasilicate as main crystal phase and comprises more than 10 vol.-% lithium metasilicate crystals.

5. Blank according to claim 3, in which the lithium metasilicate glass ceramic comprises lithium metasilicate as main crystal phase and comprises more than 20 vol.-% lithium metasilicate crystals.

6. Blank according to claim 1, in which the lithium silicate glass, the lithium silicate glass with nuclei, and the lithium metasilicate glass ceramic comprise at least one of the following components in the given amounts:

| Component | wt.-% |
| --- | --- |
| $SiO_2$ | 50.0 to 80.0 |
| $Li_2O$ | 6.0 to 20.0 |
| $Me(I)_2O$ | 0 to 10.0, |
| $Me(II)O$ | 0 to 12.0, |
| $Me(III)_2O_3$ | 0 to 8.0, |
| $Me(IV)O_2$ | 0 to 8.0, |
| $Me(V)_2O_5$ | 0 to 8.0, |
| $Me(VI)O_3$ | 0 to 8.0, |
| nucleating agent | 0 to 8.0, , | wherein
$Me(I)_2O$ is selected from $Na_2O$, $K_2O$, $Rb_2O$, $Cs_2O$ or mixtures thereof,
$Me(II)O$ is selected from CaO, BaO, MgO, SrO, ZnO and mixtures thereof,
$Me(III)_2O_3$ is selected from $Al_2O_3$, $La_2O_3$, $Bi_2O_3$, $Y_2O_3$, $Yb_2O_3$ and mixtures thereof,
$Me(IV)O_2$ is selected from $ZrO_2$, $TiO_2$, $SnO_2$, $GeO_2$ and mixtures thereof,
$Me(V)_2O_5$ is selected from $Ta_2O_5$, $Nb_2O_5$ and mixtures thereof,
$Me(VI)O_3$ is selected from $WO_3$, $MoO_3$ and mixtures thereof, and
nucleating agent is selected from $P_2O_5$, metals and mixtures thereof.

7. Blank according to claim 6, in which the lithium silicate glass, the lithium silicate glass with nuclei, and the lithium metasilicate glass ceramic comprise at least one of the following components in the given amounts:

| Component | wt.-% |
| --- | --- |
| $SiO_2$ | 65.00 to 75.00 |
| $Li_2O$ | 14.00 to 16.00 |
| $K_2O$ | 2.00 to 5.00 |
| SrO and CaO | 0 to 2.00 |
| MgO | 0 to 2.00 |
| ZnO | 0 to 2.00 |
| $Al_2O_3$ | 1.50 to 3.50 |
| $La_2O_3$ | 0 to 2.00 |
| $ZrO_2$ | 0 to 4.00 |
| $P_2O_5$ | 2.50 to 4.00. |

8. Blank according to claim 6, in which the following components are present in the given amounts:

| Component | wt.-% |
| --- | --- |
| $SiO_2$ | 50.0 to 80.0 |
| $Li_2O$ | 6.0 to 20.0 |
| $Me(I)_2O$ | 0.1 to 10.0 |
| $Me(II)O$ | 0.1 to 12.0 |

-continued

| Component | wt.-% |
| --- | --- |
| $Me(III)_2O_3$ | 0.1 to 8.0 |
| $Me(IV)O_2$ | 0.1 to 8.0 |
| $Me(V)_2O_5$ | 0.1 to 8.0 |
| $Me(VI)O_3$ | 0.1 to 8.0 |
| nucleating agent | 0.1 to 8.0. |

9. Blank according to claim 1, which has a holding means for a processing device, wherein the holding means consists of metal or plastic.

10. Method of using the blank according to claim 1 comprising producing a dental restoration from the blank, wherein the dental restoration comprises a crown, abutment, abutment crown, inlay, onlay, veneer, shell, bridge or overstructure.

11. Process for producing the blank with layers of lithium silicate glass, lithium silicate glass with nuclei or lithium metasilicate glass ceramic according to claim 1, in which
(i) monolithic layers of lithium silicate glass, lithium silicate glass with nuclei or lithium metasilicate glass ceramic are arranged on top of one another and
(ii) the layers are bonded to one another.

12. Process according to claim 11, in which layers of lithium silicate glass or lithium silicate glass with nuclei are converted to layers of lithium silicate glass with nuclei or lithium metasilicate glass ceramic and are converted by at least one heat treatment.

13. Process according to claim 12, in which layers of lithium silicate glass or lithium silicate glass with nuclei are by at least one heat treatment bonded to one another and converted to layers with lithium metasilicate glass ceramic in order to produce a blank with layers of lithium metasilicate glass ceramic.

14. Process according to claim 11, in which
(a1) a monolithic layer is applied in the form of a melt to another monolithic layer.

15. Process according to claim 14 in which monolithic layers of lithium silicate glass are used.

16. Process according to claim 15, in which one monolithic layer has a temperature of from 1100 to 1500° C. and the other monolithic layer has a temperature of from 400 to 600° C.

17. Process according to claim 11, in which
(b1) the monolithic layers arranged on top of one another are heated to a temperature of at least 500° C.

18. Process according to claim 17, in which in step (b1) the layers are pressed together at a pressure of 0.01 to 4.0 MPa.

19. Process according to claim 17, in which the surfaces facing one another of the layers are smoothed.

20. Process according to claim 17, in which
(b1) the monolithic layers arranged on top of one another are heated to a temperature in the range of from 550 to 750° C.

21. Process according to claim 11, in which
(c1) a bonding means is provided between the monolithic layers.

22. Process according to claim 21, in which the bonding means is a glass solder, a crystallizing glass solder, a glass ceramic solder or an adhesive.

23. Blank for dental purposes which has at least 2 layers, bonded to one another, of lithium disilicate glass ceramic, wherein the layers differ in colour and the layers are monolithic.

24. Blank according to claim 23, in which the lithium disilicate glass ceramic comprises lithium disilicate as main crystal phase and comprises more than 30 vol.-% lithium disilicate crystals.

25. Blank according to claim 24, in which the lithium disilicate glass ceramic comprises lithium disilicate as main crystal phase and comprises more than 40 vol.-% lithium disilicate crystals.

26. Blank according to claim 24, in which the lithium disilicate glass ceramic comprises lithium disilicate as main crystal phase and comprises more than 50 vol.-% lithium disilicate crystals.

27. Process for producing the blank with layers of lithium disilicate glass ceramic according to claim 23, in which
(iii) a blank with layers of lithium silicate glass, lithium silicate glass with nuclei or lithium metasilicate glass ceramic is subjected to at least one heat treatment in order to convert the lithium silicate glass, the lithium silicate glass with nuclei or the lithium metasilicate glass ceramic to lithium disilicate glass ceramic.

28. Process according to claim 27, in which a blank with layers of lithium silicate glass with nuclei or with layers of lithium metasilicate glass ceramic is subjected to the heat treatment.

29. Process according to claim 27, in which the heat treatment is carried out at a temperature of at least 750° C.

30. Process according to claim 29, in which the heat treatment is carried out at a temperature in the range of from 750 to 950° C.

31. Blank according to claim 23, in which the lithium disilicate glass ceramic comprises at least one of the following components in the given amounts:

| Component | wt.-% |
| --- | --- |
| $SiO_2$ | 50.0 to 80.0 |
| $Li_2O$ | 6.0 to 20.0 |
| $Me(I)_2O$ | 0 to 10.0, |
| $Me(II)O$ | 0 to 12.0, |
| $Me(III)_2O_3$ | 0 to 8.0, |
| $Me(IV)O_2$ | 0 to 8.0, |
| $Me(V)_2O_5$ | 0 to 8.0, |
| $Me(VI)O_3$ | 0 to 8.0, |
| nucleating agent | 0 to 8.0, , | wherein
$Me(I)_2O$ is selected from $Na_2O$, $K_2O$, $Rb_2O$, $Cs_2O$ or mixtures thereof,
$Me(II)O$ is selected from CaO, BaO, MgO, SrO, ZnO and mixtures thereof,
$Me(III)_2O_3$ is selected from $Al_2O_3$, $La_2O_3$, $Bi_2O_3$, $Y_2O_3$, $Yb_2O_3$ and mixtures thereof,
$Me(IV)O_2$ is selected from $ZrO_2$, $TiO_2$, $SnO_2$, $GeO_2$ and mixtures thereof,
$Me(V)_2O_5$ is selected from $Ta_2O_5$, $Nb_2O_5$ and mixtures thereof,
$Me(VI)O_3$ is selected from $WO_3$, $MoO_3$ and mixtures thereof, and
nucleating agent is selected from $P_2O_5$, metals and mixtures thereof.

32. Blank according to claim 23, in which the lithium disilicate glass ceramic comprises at least one of the following components in the given amounts:

| Component | wt.-% |
| --- | --- |
| $SiO_2$ | 65.00 to 75.00 |
| $Li_2O$ | 14.00 to 16.00 |
| $K_2O$ | 2.00 to 5.00 |
| SrO and CaO | 0 to 2.00 |
| MgO | 0 to 2.00 |
| ZnO | 0 to 2.00 |
| $Al_2O_3$ | 1.50 to 3.50 |
| $La_2O_3$ | 0 to 2.00 |
| $ZrO_2$ | 0 to 4.00 |
| $P_2O_5$ | 2.50 to 4.00. |

33. Process for producing a dental restoration, in which
(d1) a blank with layers of lithium silicate glass, lithium silicate glass with nuclei or lithium metasilicate glass ceramic is given the shape of the dental restoration by machining, wherein the layers differ in colour and the layers are monolithic,
(d2) at least one heat treatment is carried out in order to convert the lithium silicate glass, the lithium silicate glass with nuclei or the lithium metasilicate glass ceramic to lithium disilicate glass ceramic, and
(d3) optionally the surface of the obtained dental restoration is provided with a finish
or
(e1) a blank with layers of lithium disilicate glass ceramic is given the shape of the dental restoration by machining, wherein the layers differ in colour and the layers are monolithic, and
(e2) optionally the surface of the obtained dental restoration is provided with a finish.

34. Process according to claim 33, in which the machining is carried out with computer-controlled milling and/or grinding devices.

35. Process according to claim 33, in which the dental restoration is selected from the group of crowns, abutments, abutment crowns, inlays, onlays, veneers, shells, bridges and overstructures.

* * * * *